United States Patent
Barnhart et al.

[11] Patent Number: 5,893,869
[45] Date of Patent: Apr. 13, 1999

[54] RETRIEVABLE INFERIOR VENA CAVA FILTER SYSTEM AND METHOD FOR USE THEREOF

[75] Inventors: William H. Barnhart; Elvira V. Lang, both of Iowa City, Iowa

[73] Assignee: University of Iowa Research Foundation, Iowa City, Iowa

[21] Appl. No.: 08/802,061

[22] Filed: Feb. 19, 1997

[51] Int. Cl.⁶ .................................................. A61M 29/00
[52] U.S. Cl. .................. 606/200; 606/198; 604/264; 604/49
[58] Field of Search ........................... 606/198, 200; 604/174, 264, 280

[56] References Cited

U.S. PATENT DOCUMENTS

| | | | |
|---|---|---|---|
| 3,472,230 | 10/1969 | Fogarty | 128/328 |
| 3,908,661 | 9/1975 | Kramer | 128/305 |
| 4,425,908 | 1/1984 | Simon | 128/1 |
| 4,494,531 | 1/1985 | Gianturco | 128/1 |
| 4,564,014 | 1/1986 | Fogarty et al. | 128/344 |
| 4,573,966 | 3/1986 | Weikl et al. | 604/53 |
| 4,577,631 | 3/1986 | Kreamer | 128/334 |
| 4,585,000 | 4/1986 | Hershenson | 128/345 |
| 4,610,622 | 9/1986 | Quinnel | 431/5 |
| 4,610,662 | 9/1986 | Weikl et al. | 604/53 |
| 4,655,771 | 4/1987 | Wallsten | 623/1 |
| 4,723,549 | 2/1988 | Wholey et al. | 128/344 |
| 4,781,177 | 11/1988 | Lebigot | 128/897 |
| 4,790,812 | 12/1988 | Hawkins et al. | 604/22 |
| 4,793,348 | 12/1988 | Palmaz | 128/325 |
| 4,794,928 | 1/1989 | Kletschka | 128/344 |
| 4,832,055 | 5/1989 | Palestrant | 128/899 |
| 4,842,579 | 6/1989 | Shiber | 604/22 |
| 4,866,061 | 9/1989 | Blythin et al. | 514/250 |
| 4,873,978 | 10/1989 | Ginsburg | 128/345 |
| 4,886,061 | 12/1989 | Fischell et al. | 128/305 |
| 4,926,858 | 5/1990 | Gifford et al. | 606/159 |
| 4,957,501 | 9/1990 | Lahille et al. | 606/200 |
| 4,990,156 | 2/1991 | Lefebvre | 606/200 |
| 5,059,178 | 10/1991 | Ya et al. | 604/101 |
| 5,059,205 | 10/1991 | El-Nounou et al. | 606/200 |
| 5,092,839 | 3/1992 | Kipperman | 604/53 |
| 5,100,425 | 3/1992 | Fischell et al. | 606/159 |
| 5,102,415 | 4/1992 | Guenther et al. | 606/159 |
| 5,108,419 | 4/1992 | Reger et al. | 606/200 |
| 5,133,733 | 7/1992 | Rasmussen | 606/200 |
| 5,147,370 | 9/1992 | McNamara | 606/108 |
| 5,147,379 | 9/1992 | Sabbaghian et al. | 606/206 |
| 5,154,724 | 10/1992 | Andrews | 606/159 |
| 5,160,342 | 11/1992 | Reger et al. | 606/200 |
| 5,242,462 | 9/1993 | El-Nounou et al. | 606/200 |
| 5,300,086 | 4/1994 | Gory et al. | 606/200 |
| 5,324,304 | 6/1994 | Rasmussen | 606/200 |
| 5,329,942 | 7/1994 | Gunther et al. | 128/898 |
| 5,350,398 | 9/1994 | Pavcnik | 606/200 |
| 5,397,310 | 3/1995 | Chu et al. | 604/158 |
| 5,413,586 | 5/1995 | Dibie et al. | 606/200 |
| 5,415,630 | 5/1995 | Gory et al. | 604/53 |
| 5,531,788 | 7/1996 | Dibie et al. | 623/11 |
| 5,549,626 | 8/1996 | Miller et al. | 606/200 |

OTHER PUBLICATIONS

Nakagawa, Novuo et al.; "A Retrievable Nitinol Vena Cava Filter: Experimental and Initial Clinical Results"; Journal of Vascular and Interventional Radiology; May–Jun. 1994; pp. 507–512.

*Primary Examiner*—Wynn Wood Coggins
*Assistant Examiner*—Deborah Blyveis
*Attorney, Agent, or Firm*—Woodard, Emhardt, Naughton Moriarty & McNett

[57] ABSTRACT

A percutaneous filter system for providing temporary filtering of emboli from the blood is disclosed, the filter system including a delivery catheter having a first working access lumen and a second filter deployment/retrieval lumen containing a filtering device which is deployable therefrom. The filtering device includes a deployment/retrieval wire section and a filtering element formed at the distal end of said deployment/retrieval wire section. The filtering element is made of shape memory/superelastic material and is formed to have a distally expanding frustoconical pre-disposed shape which, when the filtering element is deployed by being extended distally from the delivery catheter through the filter deployment/retrieval lumen thereof, defines a filtering channel that is offset from said deployment/retrieval axis and extends about the extended axis of the working access lumen of the delivery catheter. When the filtering element is so deployed within a blood vessel, emboli trapped within the filtering element are funneled toward working access lumen of the delivery catheter and can easily be aspirated or otherwise removed therethrough. With the filtering element in place in its deployed position, other instrumentation may also be passed through the working access lumen of the delivery catheter and the filtering channel to gain access into the blood vessel as desired.

21 Claims, 3 Drawing Sheets

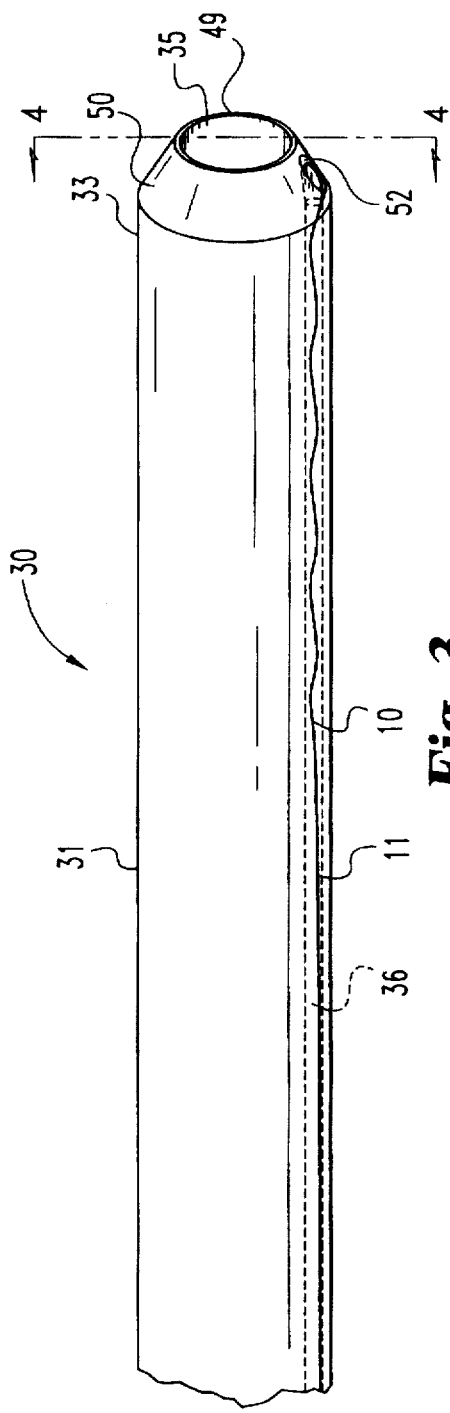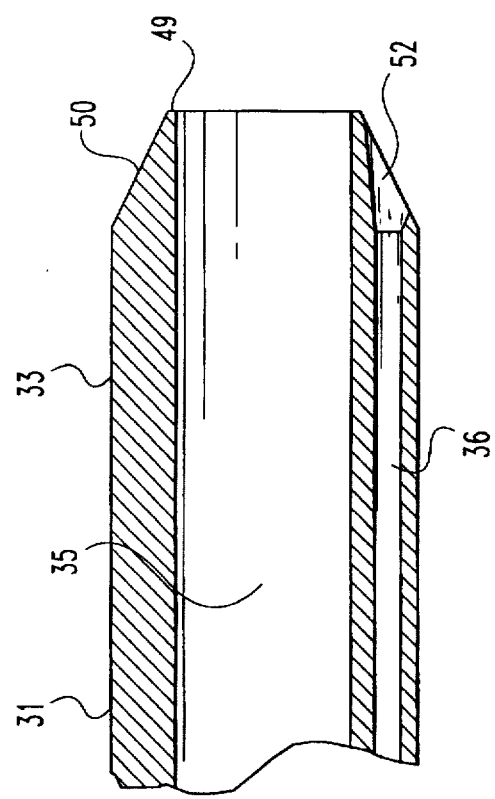

RETRIEVABLE INFERIOR VENA CAVA FILTER SYSTEM AND METHOD FOR USE THEREOF

FIELD OF THE INVENTION

This invention relates to the field of vena cava filtering devices, and more particularly to retrievable, percutaneous vena cava filters and filter systems.

BACKGROUND OF THE INVENTION

Pulmonary embolism, an obstruction of the pulmonary artery or one of its branches by a blood clot or other foreign substance, is a major cause of in-hospital death. To prevent pulmonary embolism from occurring, patients are commonly treated with anticoagulants such as Heparin and with thrombolytic agents such as Streptokinase. In some situations, however, reliance on this approach to treatment may be inappropriate where, for example, the patient is Heparin sensitive or has a high risk of internal bleeding. Also, this approach is sometimes simply ineffective in preventing recurrent pulmonary emboli.

Mechanical interruption of the inferior vena cava presents an effective alternative when chemical treatment is inappropriate or ineffective. Most devices and methods currently available for mechanically interrupting the inferior vena cava, however, carry a number of significant disadvantages. For example, applying clips or sutures to create new, multiple and reduced orifices within the inferior vena cava to trap emboli and prevent them from migrating to the lungs is an operative procedure requiring anesthesia, creates increased post-operative complications, and may ultimately cause complete occlusion of the vena cava.

Improved treatment has been effected through the development of permanently placed filters. When a permanent filter has been implanted, though, the patient must remain on anticoagulant medicine for as long as the filter is left in place. Also, over the period of time that it is left in place, a permanent filter may eventually become dislodged or become clogged, and the filter must consequently be removed or replaced. While some permanent filters are designed to be percutaneously "retrievable", they often become embedded as their anchoring hooks or protrusions become endothelialized by the vessel wall and retrieval must be done surgically.

In many cases, where long term inferior vena cava filtration is not necessary or appropriate, a temporary filter that can be readily retrieved may provide a preferable alternative. One such device, disclosed in U.S. Pat. No. 5,549,626, includes inner and outer catheters and a dome-shaped, mesh-like, collapsible filter basket mounted to the distal end of the inner catheter. In use, the inner catheter and collapsed filter basket are telescopically advanced through the lumen of the outer catheter until the basket exits the distal end of the outer catheter where it expands to its domed shape to engage the vessel walls and trap emboli. A syringe may be applied to the inner catheter to aspirate the trapped particles from the filter. Aside from the mechanical complexity of using two coaxial catheters, the mesh-like material may obstruct the flow of blood in the blood vessel more than necessary, or may be tangled or torn during introduction, placement, expansion and retrieval. The smaller inner catheter and mesh-like basket also tend to interfere with and limit the access of other instruments to the blood vessel or the placement of a permanent filter. "A Retrievable Nitinol Vena Cava Filter: Experimental and Initial Clinical Results," by Nakagawa et al. in the *Journal of Vascular and Interventional Radiology*, May–June 1994, p. 507 describes a femorally deployed temporary filter made of Nitinol which forms a frustoconical shape that decreases in diameter as the filter extends distally away from its delivery sheath in the direction toward the heart. The distal end of the filter is formed into a larger diameter, stabilizing loop, which acts to center the terminating end of the filter within the blood vessel. Unfortunately, it is difficult to reach the interior of this filter to perform aspiration, and there is a risk that emboli loosened in the attempt to aspirate or in the process of removing the filter will pass back toward the heart. While a permanent filter may be placed above the temporary filter as a precaution against such an occurrence, doing so would appear to defeat much of the purpose of utilizing a temporary filter in the first place. While this filter is in place, it is also difficult to gain access to or through the filter area with other instrumentation when the need to do so arises.

What is needed is an improved filter for trapping emboli in a blood vessel where the filter is easy to deploy and retrieve and facilitates access to the vessel at or around the filtering site, for example, to aspirate or infuse.

SUMMARY OF THE INVENTION

The present invention relates to a new percutaneous filter system for providing temporary filtering of emboli from the blood. In the following described preferred embodiment, the filter system includes a delivery catheter having a first working access lumen, and a second filter deployment/retrieval lumen containing a filtering device which is deployable therefrom. The filtering device includes a deployment/retrieval wire section and a filtering element formed at the distal end of said deployment/retrieval wire section. The filtering element is made of shape memory/superelastic material and is formed to have a pre-disposed distally expanding frustoconical shape which, when the filtering element is deployed by being extended distally from the delivery catheter through the filter deployment/retrieval lumen thereof, defines a filtering channel that is offset from said deployment/retrieval axis and extends about the extended axis of the working access lumen of the delivery catheter. When the filtering element is so deployed within a blood vessel, emboli trapped within the filtering element are funneled toward the working access lumen of the delivery catheter and can easily be aspirated or otherwise removed therethrough. With the filtering element in place in its deployed position, other instrumentation may also be passed through the working access lumen of the delivery catheter and the filtering channel to gain access into the blood vessel as desired.

It is an object of the present invention to provide an improved filtering system for filtering emboli from blood in a blood vessel.

It is also an object of the present invention to provide a blood filter for use in the inferior vena cava that provides improved access for infusion, aspiration and for other instruments at the site of filtration.

Further objects and advantages of the present invention will become apparent from the following description of the preferred embodiment.

BRIEF DESCRIPTION OF THE DRAWINGS

FIG. 3 is a perspective side view of the filter system 30 of FIG. 2 and shown in the filter delivery condition.

FIG. 4 is a side cross-sectional view of the catheter 31 of FIG. 3 along plane 3.

DESCRIPTION OF THE PREFERRED EMBODIMENT

Figure 1:
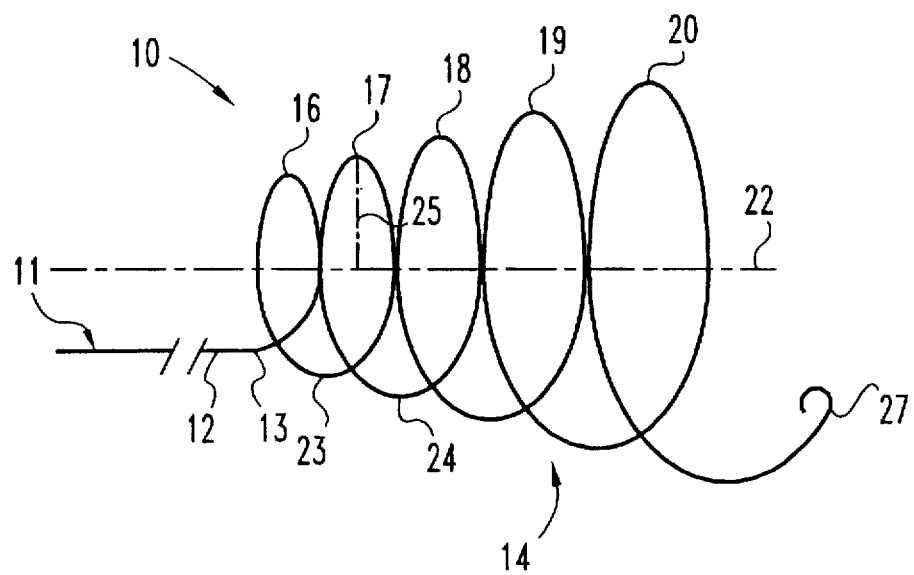
FIG. 1 is a perspective side view of a retrievable inferior vena cava filter 10 in accordance with the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, and any alterations and modifications in the illustrated device, and any further applications of the principles of the invention as illustrated therein are contemplated as would normally occur to one skilled in the art to which the invention relates.

Referring to FIG. 1, there is shown a retrievable inferior vena cava filter 10 in accordance with the preferred embodiment of the present invention. Filter 10 is a unitary length of wire 11 made from a shape memory/superelastic alloy such as the nickel-titanium alloy known as Nitinol. In the preferred embodiment, wire 11 is made from polished Nitinol monofilament wire (0.356 mm). Nitinol is a shape memory/ superelastic alloy that can be formed into a "remembered" or pre-disposed shape which it will "remember" even after the material has been substantially deformed away from this shape. When in its austenitic superelastic temperature range, this material will allow substantial deformation to occur away from its pre-disposed shape on the application of external stresses, and will return back to its pre-disposed shape when the external stresses are removed. At lower temperatures ranges, the material will not entirely regain its pre-disposed shape on the removal of external stress, but will regain the remainder of its predisposed shape upon heating back into the material's superelastic temperature range. In its lowest martensitic temperature range, the material will stay deformed after stress on it has been released, but will resume its remembered pre-disposed shape when heated back into its superelastic temperature range. For the present invention, the material to be selected for wire 11 should ideally be in its superelastic temperature range at blood temperature (37° C.) or at least be substantially superelastic at this temperature.

The "pre-disposed" shape of filter 10, as shown in FIG. 1, includes a generally straight deployment/retrieval wire section 12 which transitions at 13 into a generally expanding frustoconically shaped, spiral filtering element 14. Filtering element 14 has five turns 16–20, all of which are coaxial about a central axis 22, with central axis 22 being offset from the axis of deployment/retrieval wire 12. As shown in FIG. 1, a "turn" is here intended to mean a portion of filtering element 14 that defines a 360° path around axis 22, and the "diameter" of a turn ($D_T$) is generally defined as two times the radius of the approximate midpoint of the turn. Also as used herein, the "diameter" is measured when filtering element 14 is in the austenite phase and is not being restrained from assuming its pre-disposed shape. Thus, in FIG. 1, turn 17 is defined as that part of spiral wire 11 between points 23 and 24, and the diameter ($D_T$) of turn 17 is twice its midpoint radius ($R_T$) 25. The first, most proximal turn 16 is the smallest, and the diameter of each turn 17–20 is successively larger than that of turn 16, with the diameter of the most distal turn 20 being the greatest and chosen to approximate or exceed the diameter of the blood vessel at the desired location for placement. In this way, turn 20 attempts to expand against the inner wall of the blood vessel and stabilize filter 10. In one embodiment, the diameters of turns 16 and 20 are approximately 10 mm and 28 mm, respectively, and the axial distance between turns 16 and 20 is about 3 cm. These measurements may vary, however, with the diameter of the turns, the number of turns or other appropriate factors. It is to be understood that in alternative embodiments filtering element 14 may have fewer or greater turns than shown herein. Preferably, though, the number of turns should be between 4 and 8. Also, filtering element 14 may be formed to assume various other configurations as well, such as a "horn" or "dome" shape, which serve to collect emboli for removal through working access channel 35.

The distal end of filtering element 14 is curved around to form a loop 27 which creates a blunt surface thereat. Thus, when filtering element 14 is deployed as described below, the looped distal end 27 of filtering element 14 is much less likely to snag, erode or perforate the vena cava wall as opposed to an un-looped wire end.

Figure 5:
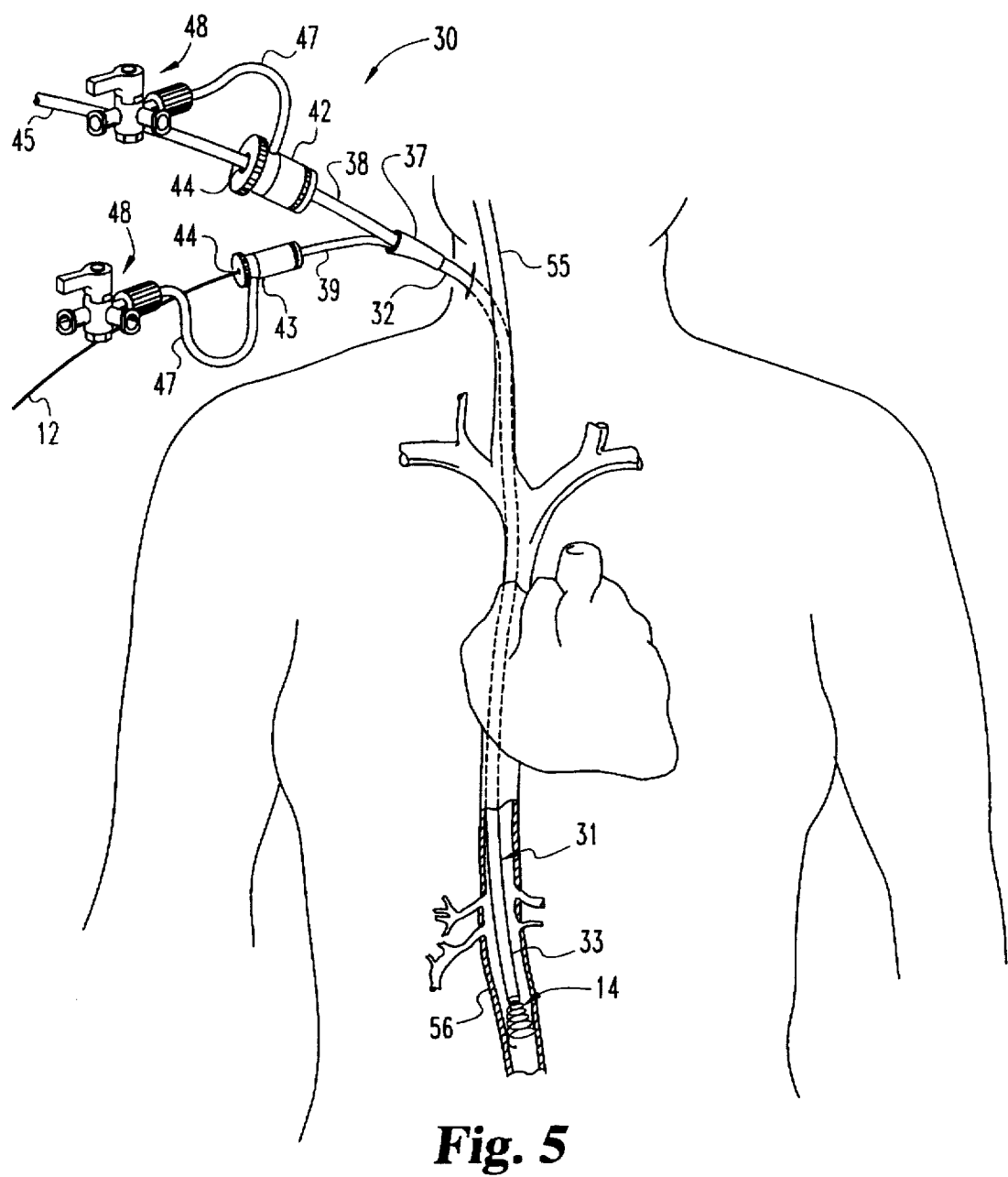
FIG. 5 is a diagramatic view of a human body showing the filter system 30 advanced to the inferior vena cava and in the deployed condition.

Referring to FIGS. 2–5, there is shown a retrievable inferior vena cava filter system 30 that includes the retrievable inferior vena cava filter 10 and a delivery catheter 31. Catheter 31 defines a first working access lumen 35 which is sized to permit a catheter or other access instrument to extend therethrough to access the region at the distal end of the catheter. Catheter 31 also defines a second filter deployment/retrieval lumen 36 which is sized to receive wire 11 for advancement and retrieval therethrough. As shown in FIG. 3, filter deployment/retrieval lumen 36 is intended to be large enough to allow wire 11 to be easily advanced and withdrawn therethrough in a manner to be described below. The diameter of lumen 36 is exaggerated in FIGS. 2–4 relative to wire 11 for illustration and discussion of the present invention. The working access lumen 35 is then made to be as large as possible relative to the inner diameter of filter deployment/retrieval lumen 36 and the outer diameter of the catheter 31 while still maintaining the desired characteristics of a catheter 31 that is intended to be introduced and advanced through the jugular and into the inferior vena cava, as shown in FIG. 5, such as high flexibility, good pushability, good torqueability, high resiliency, and a low coefficient of friction. The relative importance of each of these characteristics may vary with other variables such as patient type and other technological characteristics and advances. In one embodiment, catheter 31 is a 16 Fr catheter with the diameter of lumen 35 being large enough to receive a 9 Fr catheter, and with the diameter of lumen 36 being approximately 0.016 in. (0.406 mm) to easily receive a 0.014 in. (0.356 mm) diameter wire 11. Catheter 31 may be made of polyethylene or polyurethane or any other appropriate material known in the art for a catheter used as described herein. As is known in the art, catheter 31 may be coated or treated with an anticoagulant to prevent thrombus from forming thereon.

Figure 2:
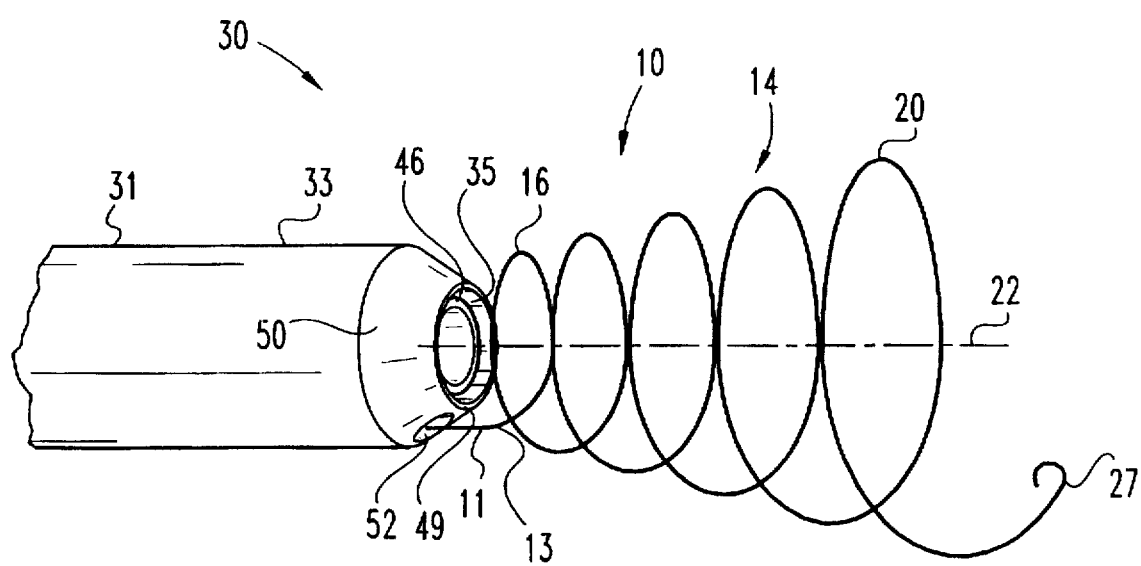
FIG. 2 is a perspective side view of the distal end of a retrievable inferior vena cava filter system 30 including a delivery catheter 31 and the filter 10 of FIG. 1 shown in the deployed condition, in accordance with the preferred embodiment of the present invention.

At its proximal end 32, catheter 31 is joined at a y-fitting 37 to a first and second tube 38 and 39, respectively, each tube having a lumen that is in fluid tight communication with lumens 35 and 36, respectively. Adapters 42 and 43 are connected to the proximal ends of tubes 38 and 39, respectively. In one embodiment, adapters 42 and 43 each consist of a Check-Flo® adapter from Cook, Incorporated of Bloomington, Ind. Each adapter 42 and 43 has a valved access opening 44 that is in communication with the lumen of the corresponding tube, 38 and 39, and the corresponding lumen 35 and 36. Up to a 9 Fr catheter or instrument 45 may be inserted through opening 44 and advanced through working access lumen 35 until the distal end 46 of such catheter or instrument 45 reaches the distal end 33 of catheter 31 (FIG. 2). Catheter 45 may be of the type used to deliver medication (such as an anticoagulant or thrombolytic agent) to the access site at the distal end 33 of catheter 31, or it could be of the type having its proximal end connected to a vacuum source to aspirate emboli as described herein. The valved access opening 44 of each Cook Check-Flo® adapter has a self-adjusting seal that prevents blood reflux and air aspiration during introduction of catheters or instruments. Each adapter also has a side connection line 47 that connects in communication with a three-way stop-cock 48 that can be used as a second infusion line.

Referring to FIGS. 2–4, the distal end of catheter 31 terminates at leading edge 49 that is substantially orthogonal to the axis of both catheter 31 and working access lumen 35 (this is best shown in FIG. 4 which is a cross-sectional view along plane 3 of the embodiment in FIG. 3). The distal end of catheter 31 is tapered at 50. In addition to facilitating insertion and advancement of the catheter in the blood vessel, tapered surface 50 further serves to facilitate deployment of filter 14 from filter deployment/retrieval lumen 36, and retraction there back into when filter 14 is to be retrieved. The distal end of filter deployment/retrieval lumen 36 defines a widened opening 52 to further facilitate deployment and retraction of filter 10.

As described herein, the axis 22 of filtering element 14 is offset from the axis of deployment/retrieval wire 12 so that when filter 10 extends from the distal end 33 of catheter 31, as shown in FIG. 2, axis 22 of filtering element 14 assumes its pre-disposed shape to extend about the extended axis of working access lumen 35. In this configuration, filtering element 14 defines a "filtering channel" extending about the extended axis of working access lumen 35. Preferably, the defined filtering channel should be sized to be at least as large as the diameter of working access lumen 35. When filtering element 14 is so deployed within a blood vessel, emboli trapped within filtering element 14 are funneled toward working access lumen 35 of delivery catheter 31 with working access lumen 35 providing access to the area within filtering element 14 for direct aspiration of trapped emboli therefrom. When filtering element 14 has been so deployed, catheter 31 also serves as a centering base for the proximal base end of filtering element 14.

In use, filter system 30 is percutaneously inserted through the jugular vein 55 and advanced to the desired location at the inferior vena cava 56 using the Seldinger technique. Under fluoroscopy, catheter 31 is introduced into vein 55 and advanced over a wire guide to the infrarenal vena cava 56 and then to a point approximately 4 cm past the desired filter deployment location.

With the leading edge 49 of catheter 31 advanced about 4 cm past the desired deployment location as observed under fluoroscopy, the operator now slowly withdraws catheter 31 while holding wire 12 steady outside of the body, in essence thereby ejecting filtering element 14 from the distal end of catheter 31. Loop 27 at the distal end of the filtering element 14 presents only a blunt surface which helps avoid an otherwise pointed distal end of the wire from eroding or puncturing the vessel wall. Owing to the shape memory/ superelastic properties of the Nitinol material from which it is made, filtering element 14 resumes its preformed shape as it is advanced from the distal end of catheter 31. While the deployment technique may vary from one operator to another, the operator may now perform some combination of further withdrawing the catheter 31 and advancing the filter 10 to complete the deployment of filtering element 14 to the desired location shown in FIG. 5 (and in enlarged fashion in FIG. 2). Once filtering element 14 is deployed into the desired location, injection of contrast medium through either lumen 35 or 36 (via auxiliary stop-cocks 48) enables the operator to confirm the proper positioning of filtering element 14. The proximal end of deployment/retrieval wire 12 may then be pulled, pushed and/or twisted to refine the positionment of filtering element 14 and then fixed thereat with respect to catheter 31 by tightening the Check-Flo® adapter 43.

In this deployed condition, the most proximal turn 16 has a diameter that is slightly larger than the outer diameter of the distal end of catheter 31. Further, the axis 22 of turns 16–20 is substantially coexistant with the axis of lumen 35. As seen in FIG. 5, because the most distal and largest turn 20 is sized approximately the same or larger than the inner diameter of infrarenal vena cava 56, and because the adjacent proximal turns 19, 18, 17 and 16 are successively smaller, emboli traveling toward the heart at the infrarenal vena cava become trapped in filtering element 14 and are funneled toward working access lumen 35. A catheter 45 that is connected at its proximal end to a suction device may be advanced through working access lumen 35 and used to aspirate emboli trapped by filtering element 14. It is further contemplated that working access lumen 35 may be used to provide working access for other instrumentation as well. At any time while catheter 31 is in the appropriate position within the inferior vena cava, anticoagulants such as Heparin or thrombolytic agents such as Streptokinase may also be introduced, if desired, through either lumen 35 or 36 via the auxiliary stop-cocks 48.

When filter 10 is to be withdrawn, some combination of advancing catheter 31 and withdrawing filter 10 may be performed to pull filtering element 14 back into filter deployment/retrieval lumen 36. Owing to the superelastic property of the Nitinol material from which is it made, filtering element 14 may be easily withdrawn back into filter deployment/retrieval lumen 36, reassuming a restrained generally straightened shape within lumen 36, and may be redeployed, if desired, to again reassume its predisposed expanding frustoconical shape for filtering within the blood vessel. Further reduction of frictional effects may be achieved by coating the exterior of wire 11 with friction-retarding coatings known in the art.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A filtering system for filtering emboli from blood within a blood vessel, said filtering system comprising:

a delivery catheter having a first working access lumen defining a working access axis, and a second filter deployment/retrieval lumen defining a filter deployment/retrieval axis; and a filtering device receivable within said filter deployment/ retrieval lumen, said filtering device including a deployment/retrieval wire section and a filtering element formed at the distal end of said deployment/retrieval wire section, said filtering element being made of shape memory/superelastic material and being formed to have a pre-disposed shape which, when said filtering element has been deployed by being extended distally from said delivery catheter through said filter deployment/retrieval lumen thereof, defines a filtering channel that is offset from said deployment/retrieval axis and which extends about the extended axis of the working access lumen of the delivery catheter, whereby when said filtering element is so deployed within a blood vessel, emboli trapped within the filtering element are funneled toward the working access lumen of said delivery catheter for removal therethrough.

2. The filtering system for filtering emboli from blood within a blood vessel of claim 1 wherein the filtering channel defined by said filtering element is at least as large as the diameter of said working access lumen of said delivery catheter.

3. The filtering system for filtering emboli from blood within a blood vessel of claim 1 wherein said filtering element is generally expanding in the distal direction away from said delivery catheter.

4. The filtering system for filtering emboli from blood within a blood vessel of claim 1 wherein said filtering element forms a generally frustoconical shape.

5. The filtering system for filtering emboli from blood within a blood vessel of claim 1 wherein the filter axis is offset from said deployment/retrieval wire an amount approximately equal to the distance between the axes of the filter deployment/retrieval lumen and the working access lumen at the distal end of said catheter.

6. The filtering system for filtering emboli from blood within a blood vessel of claim 1 wherein the diameter of the working access lumen is substantially larger than the diameter of the filter deployment/retrieval lumen.

7. The filtering system for filtering emboli from blood within a blood vessel of claim 1 wherein said filtering element includes a series of turns and wherein each turn successively increases in diameter from the most proximal to the most distal of said turns.

8. The filtering system for filtering emboli from blood within a blood vessel of claim 7 wherein there are a total of between 4 to 8 of said turns.

9. The filtering system for filtering emboli from blood within a blood vessel of claim 8 wherein the diameter of the most distal of said turns is greater than the inner diameter of the blood vessel.

10. The filtering device for filtering emboli from blood within a blood vessel of claim 1 wherein the shape memory/superelastic alloy from which said filtering element is made is in its superelastic temperature range at blood temperature.

11. The filtering system for filtering emboli from blood within a blood vessel of claim 10 wherein said filtering device is an integrally formed, one-piece wire made of Nitinol.

12. The filtering system for filtering emboli from blood within a blood vessel of claim 1 wherein the filter deployment/retrieval lumen is enlarged at the distal end of said catheter.

13. The filtering system for filtering emboli from blood within a blood vessel of claim 1 wherein said catheter has an outer surface that is tapered at the distal end of said catheter.

14. A method for filtering emboli from blood within a blood vessel, said method comprising the steps of:

introducing a delivery catheter into the blood vessel, the delivery catheter having a first working access lumen defining a working access axis, and a second filter deployment/retrieval lumen defining a filter deployment/retrieval axis, and a filtering device received within the filter deployment/retrieval lumen, the filtering device including a deployment/retrieval wire section and a filtering element formed at the distal end of the deployment/retrieval wire section, the filtering element being made of shape memory/superelastic material and being formed to have a pre-disposed shape which, when the filtering element has been deployed by being extended distally from the delivery catheter through the filter deployment/retrieval lumen thereof, defines a filtering channel that is offset from the deployment/retrieval axis and which extends about the extended axis of the working access lumen of the delivery catheter;

advancing the distal end of the delivery catheter to a desired location within the blood vessel; and advancing the filtering device relative to the delivery catheter so that the filtering element exits the filter deployment/retrieval lumen at the distal end of the catheter and expands into its pre-disposed shape within the blood vessel, whereby emboli trapped within the filtering element are funneled toward the working access lumen of the delivery catheter for removal therethrough.

15. The method for filtering emboli from blood within a blood vessel of claim 14 in which the filtering channel defined by said filtering element is at least as large as the diameter of the working access lumen of the delivery catheter.

16. The method for filtering emboli from blood within a blood vessel of claim 14 in which the filtering element is generally expanding in the distal direction away from the delivery catheter.

17. The method for filtering emboli from blood within a blood vessel of claim 14 in which the filtering element forms a generally frustoconical shape.

18. The method for filtering emboli from blood within a blood vessel of claim 14 further includes the step of applying suction to the desired location through the working access lumen.

19. The method for filtering emboli from blood within a blood vessel of claim 18 wherein said applying suction step includes advancing a catheter having proximal and distal ends through the working access lumen, said catheter having a suction source connected at its proximal end.

20. The method for filtering emboli from blood within a blood vessel of claim 14 which additionally includes the step of passing another instrument through the working access lumen of the delivery catheter and the filtering channel to gain access into the blood vessel.

21. The method for filtering emboli from blood within a blood vessel of claim 14 in which the shape memory/superelastic alloy from which the filtering element is made is in its superelastic temperature range at blood temperature.

* * * * *